United States Patent [19]

Wei et al.

[11] Patent Number: 4,801,612

[45] Date of Patent: Jan. 31, 1989

[54] METHOD OF INHIBITING INFLAMMATORY RESPONSE

[75] Inventors: Edward T. Wei, El Cerrito; Juliann G. Kiang, Benicia, both of Calif.

[73] Assignee: Regents of the University of California, Berkeley, Calif.

[21] Appl. No.: 881,321

[22] Filed: Jul. 3, 1986

[51] Int. Cl.$^4$ .............................................. A61K 37/40
[52] U.S. Cl. ...................................................... 514/12
[58] Field of Search ........................................... 514/12

[56] References Cited

U.S. PATENT DOCUMENTS

| | | | |
|---|---|---|---|
| 3,980,778 | 9/1976 | Ayer et al. | 424/245 |
| 4,361,553 | 11/1982 | Loh et al. | 514/12 |
| 4,404,198 | 9/1983 | Kelly | 424/235 |
| 4,415,558 | 11/1983 | Vale, Jr. et al. | 514/12 |
| 4,481,191 | 11/1984 | Wei et al. | 514/12 |
| 4,489,163 | 12/1984 | Rivier et al. | 436/86 |
| 4,528,189 | 7/1985 | Lederis et al. | 514/12 |
| 4,533,654 | 8/1985 | Lederis et al. | 514/12 |
| 4,579,844 | 4/1986 | Rovee et al. | 514/171 |

OTHER PUBLICATIONS

Litchfield and Wilcoxon, *J. Pharmacol. Exp. Ther.*, pp. 99–113 (1949).
Siegmund et al., *Proceedings of the Society for Experimental Biology and Medicine* 95, pp. 729–731 (1957).
Janssen et al., *Arzneim. Forschung* 13, pp. 502–507 (1963).
Melchiorri and Negri, *Regulatory Peptides* 2, pp. 1–13 (1981).
Saria, *Br. J. Pharmac.* 82, pp. 217–222 (1984).
Esch et al., *BBRC*, vol. 122, pp. 899–905 (1984).
Ling et al., *BBRC*, vol. 122, pp. 1218–1224 (1984).
Stern et al., *Arch. Derm.* 121, pp. 508–512 (1985).
Kiang and Wei, *Eur. J. Pharmacol.* 114, pp. 111–112 (1985).
Patthy et al., *Proc. Natl. Acad. Sci*, vol. 82, pp. 8762–8766 (1985).

*Primary Examiner*—Delbert R. Phillips
*Attorney, Agent, or Firm*—Majestic, Gallagher, Parsons & Siebert

[57] ABSTRACT

Many malignant neoplasias are treated by radiation therapy which can result in painful inflammation of the covering skin and/or mucosal membranes. Similarly, skin disorder patients receiving U.V. treatment may experience an inflammatory response.

Certain neuropeptides have been discovered to have the unusual properties of preventing, or inhibiting, the edema and protein extravasation of skin and mucosal membrane injuries due to thermal or radiation assault or exposure to trauma or noxious agents. A method for inhibiting an inflammatory response in the skin or mucosal membranes of a patient is provided in which a therapeutically effective amount of a neuropeptide, such as Corticotropin Releasing Factor ("CRF") or its analogs, is administered.

11 Claims, 2 Drawing Sheets

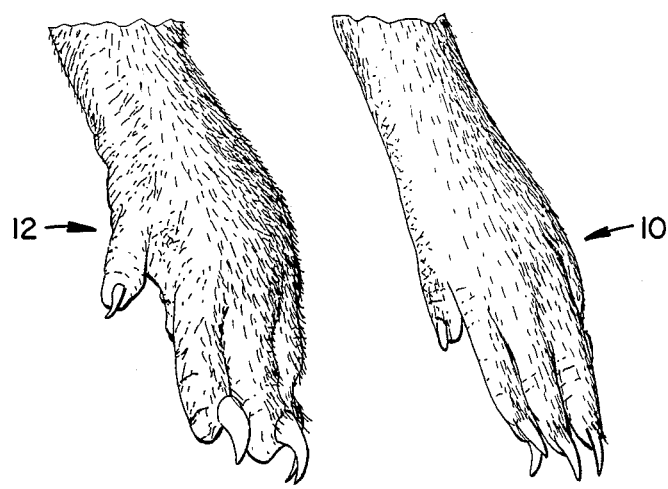
FIG.__1.
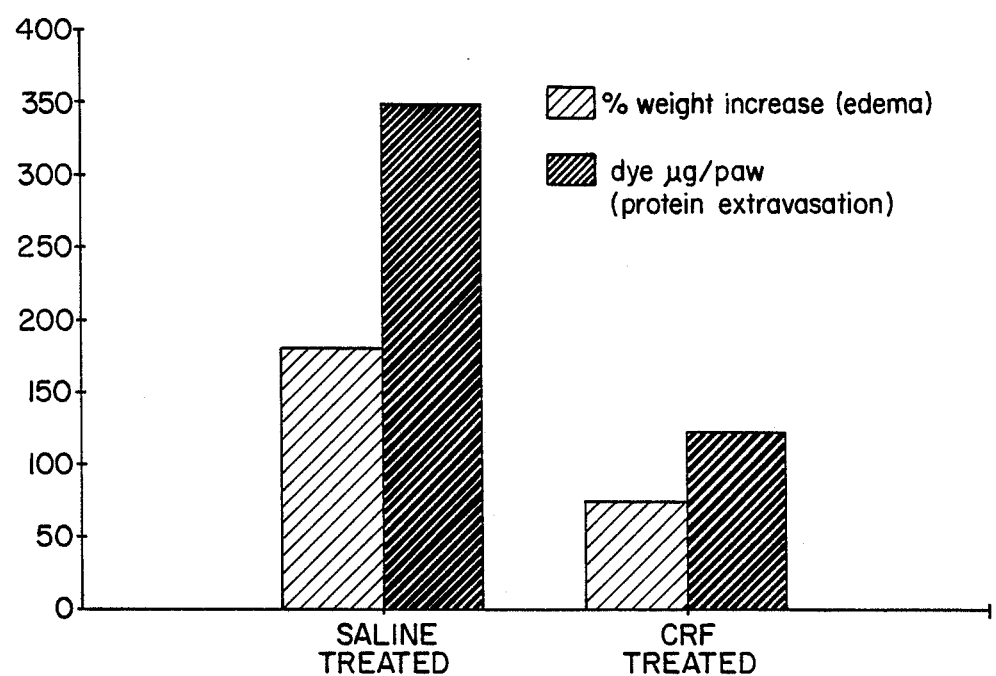
FIG.__2.

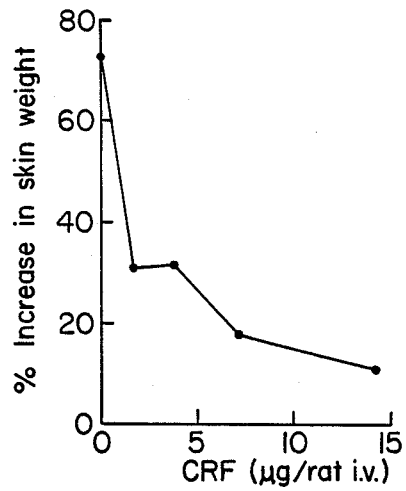
FIG._3.
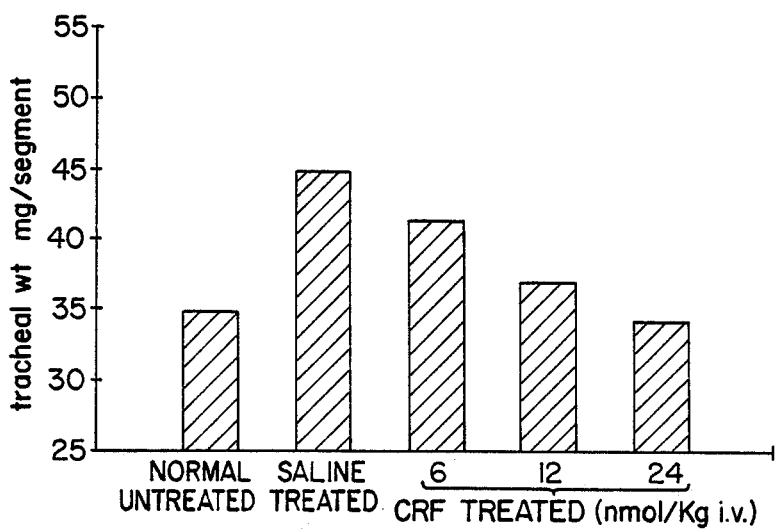
FIG._4.
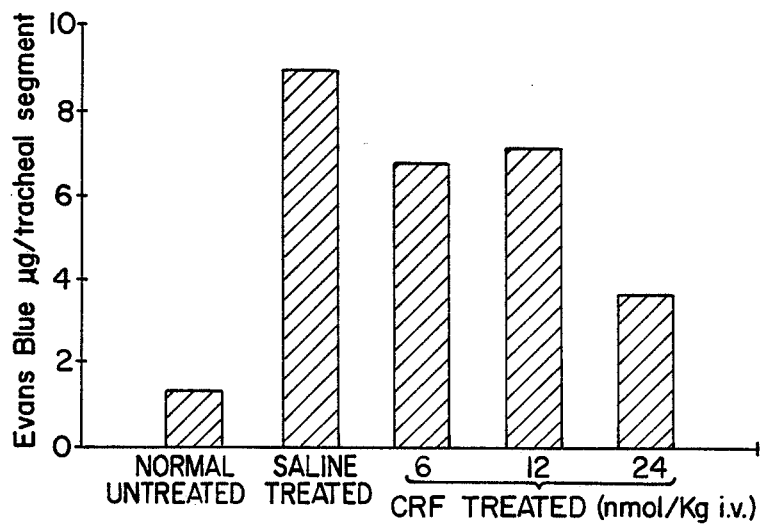
FIG._5.

METHOD OF INHIBITING INFLAMMATORY RESPONSE

FIELD OF THE INVENTION

This invention generally relates to a method of inhibiting an inflammatory response of skin or mucosal membranes to injury, and more particularly to the use certain neuropeptides, particularly of Corticotropin Releasing Factor and its analogs, in attenuating inflammation of the skin and mucosal membranes following thermal or radiation assault or exposure to noxious agents.

This invention was made with Government support under Grant No. DA-00091 with the U.S. Public Health Service, Department of Health and Human Services, and the University of California. The Government has certain rights in this invention.

BACKGROUND OF THE INVENTION

Inflammation is signaled by redness, swelling, heat and pain as a reaction of the body against injury or assault. A variety of chemicals have been implicated as chemical mediators of the inflammatory reaction, including histamine, serotonin, kinins, prostaglandins, leukotrienes, and, from nerve endings, substance P. Mediators of the acute inflammatory reaction seem to play roles in one or more of increasing vascular permeability, attracting leucocytes, producing pain, local edema and necrosis.

Each of the four signs of inflammation has been used by pharmacologists to establish methods for the detection and definition of anti-inflammatory substances. The inhibition of an induced edema, usually in the paw of a rat, has been a preferred method. Edemas can be induced in the rat or guinea pig models by means of UV radiation, irritants or heat. For example, thermal injury to the skin of animals produces an inflammatory response which is accompanied by erythema Erythema is part of the immediate response to injury which is followed by a delayed edematous response There are steroid and non-steroid, anti-inflammatory drugs known to the art. U.S. Pat. No. 4,579,844, inventors Rovee et al., issued Apr. 1, 1986, discloses topically treating an inflammatory condition of the skin by use of the prostaglandin synthetase inhibitor concurrently with a corticosteroid. U.S. Pat. No. 4,404,198, inventor Kelley, issued Sept. 13, 1983, discloses the topical application of a composition including phenyl salicylate to treat inflammation. U.S. Pat. No. 3,980,778, inventors Ayer et al., issued Sept. 14, 1976, discloses a steroid for use in the topical, oral or parenteral treatment of skin and mucous membrane inflammations. Ibuprofen (a known anti-inflammatory agent) has been tested in connection with UV-B-induced inflammation, but was found to have limited usefulness in treating sunburn reaction and is only somewhat more effective than placebo for the relief of symptoms associated with UV-B-induced inflammation after high dose UV-B phototherapy for psoriasis. Stern et al., *Arch. Derm.*, 121, pp. 508–512 (1985).

There are difficulties with presently used anti-inflammatory agents. Steroids, for example, are effective in reducing inflammation, but have some adverse side effects and tend to act fairly slowly.

Corticotropin Releasing Factor (hereinafter "CRF") is a 41 amino acid neuropeptide that is present in brain and the peripheral nerve endings, and stimulates ACTH release from pituitary cells. U.S. Pat. No. 4,489,163, inventors Rivier et al., issued Dec. 18, 1984, discloses rat CRF and its analogs. Human CRF has the same sequence as rat CRF. The amino acid sequence of both human and rat CRF is illustrated below:

Ser—Glu—Glu—Pro—Pro—Ile—Ser—Leu—Asp—Leu—Thr—
Phe—His—Leu—Leu—Arg—Glu—Val—Leu—Glu—Met—
Ala—Arg—Ala—Glu—Gln—Leu—Ala—Gln—Gln—Ala—His—
Ser—Asn—Arg—Lys—Leu—Met—Glu—Ile—Ile—NH$_2$

There are a number of analogs of CRF known to the art. U.S. Pat. No. 4,415,558, inventors vale, Jr. et al., issued Nov. 15, 1983, discloses the synthesis of sheep CRF, analogs, and isolation of the oCRF from ovine hypothalamic extracts. The synthetic oCRF was found to lower blood pressure. The amino acid sequence of ovine (sheep) CRF is illustrated below:

Ser—Gln—Glu—Pro—Pro—Ile—Ser—Leu—Asp—Leu—
Thr—Phe—His—Leu—Leu—Arg—Glu—Val—Leu—Glu—
Met—Thr—Lys—Ala—Asp—Gln—Leu—Ala—Gln—
Gln—Ala—His—Ser—Asn—Arg—Lys—Leu—Leu—Asp—
Ile—Ala—NH$_2$

A generally similar peptide, sauvagine, was described in *Regulatory Peptides* 2, 1-13 (1981). Sauvagine is a 40 amino acid peptide and has been reported to have biological activity in lowering blood pressure in mammals and stimulating the secretion of ACTH and β-endorphin. The amino acid sequence of sauvagine is illustrated below:

pGlu—Gly—Pro—Pro—Ile—Ser—Ile—Asp—Leu—Ser—
Leu—Glu—Leu—Leu—Arg—Lys—Met—Ile—Glu—Ile—
Glu—Lys—Gln—Glu—Lys—Glu—Lys—Gln—Gln—Ala—
Ala—Asn—Asn—Arg—Leu—Leu—Leu—Asp—Thr—
Ile—NH$_2$

U.S. Pat. No. 4,528,189, inventors Lederis et al., issued July 9, 1985, and U.S. Pat. No. 4,533,654, inventors Lederis et al., issued Aug. 6, 1985, disclose peptides similar to the rat and sheep CRF and analogs thereof, and found this white sucker and carp urotensin respectively to stimulate ACTH and to lower blood pressure. The amino acid sequence of carp urotensin is illustrated below:

H—Asn—Asp—Asp—Pro—Pro—Ile—Ser—Ile—Asp—
—Leu—Thr—Phe—His—Leu—Leu—Arg—Asn—Met—
—Ile—Glu—Met—Ala—Arg—Asn—Glu—Asn—Gln—
—Arg—Glu—Gln—Ala—Gly—Leu—Asn—Arg—Lys—
—Tyr—Leu—Asp—Glu—Val—NH$_2$

The other CRF-related peptide, white sucker urotensin, has an amino acid sequence the same as the carp urotensin, except the amino acid at the 24 position is Isoleucine and the amino acid at the 27 position is Glutamic Acid.

Ling et al., *BBRC*, Vol. 122, pp. 1218-1224 (1984), disclose the structure of goat CRF, which is the same as that for sheep CRF. Esch et al., *BBRC*, Vol. 122, pp. 899-905 (1984), disclose the structure of bovine CRF which differs from sheep and goat CRF only by one amino acid residue (number 33 which is Asparagine rather than the number 33 Serine of goat and sheep CRF). Porcine CRF has been isolated and characterized by Patthy et al., *Proc. Natl. Acad. Sci.*, Vol. 82, pp. 8762-8766 (1985). Porcine CRF shares a common amino acid sequence (residues 1-39) with rat/human CRF and differs from these only in position 40 and 41. Residue 40 can be either asparagine or isoleucine and residue 41 is phenylalanine-amide.

CRF has recently been found to inhibit the neurogenic plasma extravasation ("NPE") produced by antidromic stimulation of the rat saphenous nerve by intravenous injections of microgram per animal doses. Kiang and Wei, *Eur. J. Pharmacol.* 114, 111 (1985).

Many malignancies, such as brain tumors, spinal, oral, breast and nasal cavity cancers, are treated by radiation therapy whcch often results in painful inflammation of the covering skin or mucosa. Victims of exposure to smoke, hot air and tear gas experience inflammation of the trachea, and burn or scald patients experience painful skin inflammation. Patients undergoing U.V. treatment for psoriasis can experience sunburn as a side effect. There is a need for a direct, potent and fast-acting treatment to reduce or inhibit the acute inflammatory response acting on the skin and mucosal surfaces to thermal and/or radiation injury and from noxious agents, particularly in connection with cancer patients undergoing radiation therapy, victims of fires, and patients undergoing U.V. treatment, or the like.

SUMMARY OF THE PRESENT INVENTION

It is an object of the present invention to provide a method of inhibiting inflammation of the skin and mucosal membranes from thermal or radiation injury or from noxious substances quickly and directly.

The treatment comprises administering a therapeutically effective amount of a neuropeptide, preferably Corticotropin Releasing Factor (CRF) or one of its analogs. The administration is preferably intravenous, intradermal or subcutaneous in doses from about 1 to about 200 µg/kg, more preferably about 30 µg/kg i.v. Practice of the inventive treatment substantially prevents or greatly inhibits the acute inflammatory response for patients receiving treatment, alleviates pain and discomfort, and prevents further swelling for patients already experiencing inflammation.

BRIEF DESCRIPTION OF THE DRAWINGS

In the drawings:

FIG. 1 is a perspective view illustrating the paws of two anesthetized rats, following exposure to heat trauma (58° C. for 5 min.), the rightmost one (10) of which was treated in accordance with invention and the leftmost one (12) of which was a control;

FIG. 2 is a graphic illustration of edema and protein extravasation for rat. paws where the rats had either saline or CRF administered followed by exposure to heat trauma (58° C. for 5 min.);

FIG. 3 is a plot of heat-induced tissue edema, as measured by changes in skin weight;

FIG. 4 is a graphic illustration of edema for rat tracheas where the rats had either saline or CRF administered followed by exposure to formaldehyde vapor (1% for 10 min.); and FIG. 5 is similar to FIG. 4 but is a graphic illustration of protein extravasation in rat tracheas.

DETAILED DESCRIPTION OF THE PREFERRED EMBODIMENTS

When the skin or a mucosal surface is injured by heat, radiation or assaulted by noxious substances, it is converted from a condition of balanced fluid exchange to a state in which serum and its solutes freely pass into the surrounding tissues. Substances are released, either from nerve endings or from cells within the injured tissue, that produce increased vascular permeability. Fluids and proteins in the blood then move from the vascular compartment to the tissue compartment with pain, swelling and tissue damage as a result. Substance P is a kinin that, when released during tissue injury, produces itching, edema and extravasation of the blood constituents. Saria, *Br. J. Pharmac* 82, 217–222 (1984) reported that substance P in sensory nerve fibers contributes to the development of edema in the rat hind paw after thermal injury.

In the present invention, a neuropeptide effective to inhibit inflammation of a mammal's skin and/or mucosal membranes is administered. Preferred neuropeptides include CRF or an analog thereof used to inhibit inflammation of skin or mucosal-surfaces caused by heat or radiation injury and assault by noxious compounds. By "CRF" is meant herein mammalian Corticotropin Releasing Factor, including rat, human, beef, goat, pig or sheep Corticotropin Releasing Factor. Analogs of CRF include sauvagine, carp urotensin and sucker urotensin (all of which have been isolated from lower vertebrates) and those synthetic peptide structures analogous to CRF and these CRF-related peptides and disclosed in U.S. Pat. Nos. 4,415,558, 4,489,163, 4,553,654, and 4,528,189, incorporated herein by reference.

Mammalian CRF and sauvagine in therapeutically effective amounts have been discovered dramatically to reduce the tissue swelling and protein leakage that accompanies thermal injury to the skin. CRF is also effective against injury to the lining of the trachea (windpipe). These effects are obtained at low doses, in the µg/kg range by the intravenous route, and are of clinical benefit for many injuries that occur to the skin and to mucosal membranes, such as lining of the lungs and the trachea.

The effective neuropeptides for use in the present invention may be readily prepared by solid phase peptide synthesis techniques. The synthesis is commenced from the carboxyl terminal end of the peptide by coupling the appropriate amino acid, e.g. L-Arginine, L-Isoleucine, L-Phenylalanine or L-valine, to a suitable resin support, such as a p-methyl benzhydrylamine resin, a chloromethylated resin or a hydroxymethyl resin.

The coupling reaction is carried out with the aid of a carboxyl group activating compound, such as Dicyclohexylcarbodiimide, and with the o-amino group of of the amino acid protected with a protecting group, such as t-butyloxycarbonyl (BOC), benzyl(BZL), p-methylbenzyl (MBZL), t-amyloxycarbonyl(AOC), tosyl(TOS), o-bromobenzyloxycarbonyl(BrZ), cyclohexyl (OHEX), or dichlorobenzyl(BzlCl$_2$). Following this coupling reaction, the α-amino protecting group is removed, such as by using trifluoroacetic acid in methylene chloride, trifluoroacetic alone or HCl in dioxane, with the deprotection being carried out at a temperature between about 0° C. and room temperature. Thereafter, each succeeding amino acid in the sequence is coupled in the same manner stepwise in the desired order, culminating in the addition of the final amino acid (e.g., L-Serine, L-Asparagine or L-Glutamine) to obtain the desired peptide.

As an alternative to adding each amino acid separately to the reaction, some may be coupled prior to addition to the solid phase reactor. Each protected amino acid or amino acid sequence is introduced into the solid phase reactor in excess (about a three- or fourfold excess), and the coupling may be carried in a medium of dimethylformamide:methylene chloride 1:1, or in dimethylformamide or methylene chloride alone. The success of the coupling reaction at each stage of the synthesis may be monitored by the ninhydrin reaction.

After the final amino acid in the sequence has been coupled, the deprotection step is carried out by treatment with a reagent such as hydrogen fluoride.

When a p-methyl benzhydryl amine resin has been used as the resin support, the peptide cleaved (by treatment with a reagent such as hydrogen fluoride) from the resin will be in the carboxyl terminal amide form. When a chloromethylated resin or a hydroxymethyl resin has been used as the resin support, the peptide cleaved from the resin support will be in the form of the carboxyl terminal benzyl ester, which may then be readily converted by methods well known in the art to provide the carboxyl terminal amide form of the peptide.

Although protein extravasation produced in NPE may be initiated by the peripheral release of substance P from sensory nerve afferents, inhibition of NPE does not predict inhibition of skin or mucosal membrane inflammation caused by heat or radiation injury or exposure to noxious agents. Morphine, for example, inhibits NPE when injected shortly before electrical, antidromic stimulation of the rat saphenous nerve. However, morphine only reduces or prevents pain, and does not inhibit the swelling of the inflammatory response.

By contrast, at low doses injected either intradermally or intravenously, rat/human/sheep CRF or sauvagine is able to block the tissue swelling associated with heat injury. Moreover, rat/human CRF also prevents edema in the trachea.

Therapeutically effective doses of CRF or its analogs are at least about 0.1 $\mu$g/kg, more preferably from about 1 to about 200 $\mu$g/kg, and most preferably are from about 5 to about 100 $\mu$g/kg. A particularly preferred dose is about 30 $\mu$g/kg administered i.v. Where damage to tissues, such as skin or lungs, is severe (or a less potent neuropeptide is being administered), larger doses than about 200 $\mu$g/kg may be advisable. The dose may be infused slowly intradermally or subcutaneously, or may be injected directly into an afflicted body part. When injected locally, doses of about 10 to about 100 $\mu$g per local administration (i.e. about 0.1 to about 1 $\mu$g/kg body weight) are preferred.

The neuropeptides should be administered under the guidance of a physician. Administration is preferably by intravenous, intradermal or subcutaneous injection within about 2 hrs. before the circumstances causing an inflammatory response, during such circumstances, or after, and the active neuropeptide may be administered in combination with a pharmaceutically acceptable carrier, such as isotonic saline, phosphate buffer solution, or the like. Topical administration is not preferred, since the preferred CRF or an analog is a large molecule (e.g., 40 or 41 amino acids) and is not as efficiently delivered to the site of action as when administered by injection.

Although the peptides are generally water soluble as typically synthesized, they may be administered in the form of pharmaceutically acceptable nontoxic salts, such as acid addition salts. Illustrative acid addition salts are hydrochloride, hydrobromide, sulfate, sulphate, acetate, citrate, benzoate, succinate, malate, ascorbate, tartrate, or the like.

When the neuropeptide is being administered prior to a patient's exposure to treatment causing an inflammatory response—such as in connection with cancer patients undergoing radiation therapy or U.V. treatment for skin disorders—administration is preferably within about 1 hr. prior to the therapy, most preferably is about 10 min. before the radiation therapy. When administration is subsequent to exposure causing an acute inflammatory response, then practice of the invention will assist in alleviating pain and discomfort and will prevent further swelling.

The surprising anti-inflammatory properties of neuropeptides administered in accordance with the invention will now be exemplified by the following description of experimental methods and results. It is to be understood that the invention is not limited thereto.

Male albino rats weighing 200 to 280 g were anesthetized with sodium pentobarbital, 60 mg/kg i.p., and a right jugular vein cannulated for drug injections. Human/rat CRF (at various dosages described below) or saline, and Evans blue dye, 50 mg/kg, were injected intravenously 10 and 3 min., respectively, before immersion of the hind paw in 48° C. or 58° C. water for 5 min. The frequency of paw withdrawal from the water was then counted. Leakage of Evans blue dye into the paw skin becomes visible within 2 min. At water temperatures of 58° C., the average dye content was 364±17 $\mu$g/paw for rats receiving saline.

At the end of the exposure period, the animals were sacrificed and the dorsal skin, between the calcaneal process and phalanges, was removed from both paws, weighed, and each placed in 4 ml of formamide for 3 days at room temperature. The extracted Evans blue was quantified colorimetrically at 600 nm with readings from the untreated paw skin used as the blank values.

In another series of experiments, saline or CRF was injected intradermally into the dorsal skin of the hind paw with a Stoelting automated microsyringe, model 51219, coupled to PE-20 tubing and a 27 gauge needle. Five $\mu$l of solution was delivered at the rate of 0.29 $\mu$l/sec. The median effective dose (ED50) and 95% confidence limits of CRF for inhibiting Evans blue leakage into the skin of the paw were 0.17 (0.07–0.40) $\mu$g/rat i.d. and 3.7 (1.9–7.4) $\mu$g/rat i.v., calculated according to the method of Litchfield and Wilcoxon, *J. Pharmacol. Exp. Ther.* 96, 99 (1949). The ug/rat unit was used in order to compare the intradermal dose (given on a per rat basis) to the intravenous dose.

Protein extravasation was measured by injecting a dye into a blood compartment of the animal. The dye binds to blood proteins and when the permeability of the tissue is increased by the heat, the dye leaks into the skin of the paw. The skin of the paw was excised, the dye extracted, and the amount of dye in the skin was measured to provide an index of the skin permeability changes that accompany the heat damage. CRF reduced the degree of dye leakage into the paw relative to the saline-treated animals. In a manner analogous to that described above for administration of CRF, sauvagine was administered and paws of the anesthetized recipients exposed to water at 58° C. Saline was administered to a control group. The dose of sauvagine was 5 $\mu$g/kg given i.v. 5 min. before paw immersion.

Table I, below, illustrates Paw edema and protein extravasation data from experiments at 58° C. where rat CRF, sheep CRF, sauvagine and dynorphin (1–13) were administered in accordance with the invention as described above. In addition, other groups of rats were administered either morphine sulfate or dexamethasone, and groups of rats were administered saline as controls.

TABLE I

| Chemical Injected | Dose mg/kg i.v. | N[1] | % Weight Increase | Dye μg/paw |
|---|---|---|---|---|
| saline* | — | 8 | 135 ± 5 | 250 ± 24 |
| morphine SO₄* | 3.0 | 8 | 157 ± 12 | 290 ± 36 |
| saline* | — | 8 | 169 ± 8 | 304 ± 13 |
| dexamethasone* | 0.50 | 8 | 170 ± 14 | 375 ± 23 |
| saline* | — | 8 | 169 ± 8 | 304 ± 13 |
| sauvagine* | 0.005 | 8 | 51 ± 11 | 86 ± 18 |
| saline** | — | 12 | 176 ± 9 | 364 ± 17 |
| rCRF** | 0.028 | 8 | 83 ± 8 | 127 ± 16 |
| rCRF** | 0.112 | 8 | 67 ± 8 | 120 ± 17 |
| saline** | — | 8 | 158 ± 9 | 341 ± 11 |
| oCRF** | 0.028 | 8 | 114 ± 10 | 236 ± 20 |
| oCRF** | 0.168 | 8 | 54 ± 5 | 102 ± 11 |
| saline*** | — | 10 | 174 ± 9 | 439 ± 20 |
| dynorphin (1–13)*** | 0.94 | 7 | 194 ± 6 | 411 ± 15 |
| dynorphin (1–13)*** | 3.75 | 8 | 87 ± 17 | 223 ± 37 |

[1]Number of Subjects
*Administered 5 min. before exposure
**Administered 10 min. before exposure
***Administered 20 min. before exposure As shown by the data of Table I, above, neither morphine nor dexamethasone inhibits either edema (indicated by % weight increase) or protein extravasation (indicated by dye amount). Dexamethasone is a potent synthetic corticosteroid. It is known that ACTH releases corticosteroids from the adrfenal cortex. The failure of dexamethasone to inhibit either edema or protein extravasation in these experiments, as shown by the data of Table I, above, illustrates that the anti-inflammatory properties of CRF (and sauvagine) shown above are not by means of an ACTH mechanism via a corticosteroid release. Steroids, unlike the present invention, have limited utility in clinical practice because they can lower the threshold for infection and can also cause other undesirable side effects. By contrast to the morphine sulfate and dexamethasone, rat CRF reduced edema by about half and reduced protein extravasation by about one-third. Sheep CRF was particularly effective at 0.168 mg/kg i.v. and reduced edema by about one-third and protein extravasation by over one-third. Sauvagine, at a dose of only 5 μg/kg i.v., was about comparable to the sheep CRF at 168 μg/kg i.v. in reducing edema and was even more effective in reducing protein extravasation.

Dynorphin (1–13) is a synthetic peptide found to have substantially comparable biological activity to the naturally occurring dynorphin (1–17). Some therapeutic uses of dynorphin, particularly dynorphin (1–13) and dynorphin (1–10) amide, are described in U.S. Pat. Nos. 4,361,553, inventors Loh et al., issued Nov. 30, 1982, and 4,481,191, inventors Wei et al., issued Nov. 6, 1984, incorporated herein by reference.

As may be seen by the data in Table I, dynorphin (1–13) did reduce edema and protein extravasation at a dose of 3750 μg/kg i.v., but did not at a dose of 940 μg/kg. Thus, dynorphin is not very potent, but is therapeutically effective in accordance with the invention at a sufficient dosage.

In a manner analogous to that above described for administration of sauvagine, but with exposure to water at a temperature of 48° C., the edema of control rats (saline administered) was 72.1% + 15.4 increased skin weight while the rats treated with sauvagine had a paw skin weight increase of only 4.9% + 2.0. For measurement of protein extravasation, the dye increase of the controls was 88.6 + 17.3 μg/paw, whereas the sauvagine treated rats had a dye increase of only 13.7 + 3.5 μg/paw.

Turning to FIG. 1, rat's paw (10) is illustrative of an anesthetized rat which had been injected intravenously 10 and 3 min. with CRF (0.112 mg/kg i.v.) and Evans blue dye, respectively before immersion of the paw (10) in 58° C. water for 5 min. The paw (10) of the rat treated in accordance with the invention exhibited little blue color (i.e., substantially no protein extravasation) and substantially no swelling by contrast, the rat paw (12) of an anesthetized rat to which a comparable amount of saline (instead of CRF) and Evans blue dye had been administered i.v. 10 and 3 min. before immersing the paw in 58° C. water for 5 min. exhibited substantial protein extravasation and significant swelling.

Turning to FIG. 2, anesthetized rats were administered either saline or CRF (6 nmole/kg) i.v. One hind paw of rats from each group was placed in hot water (58° C.) for 5 min. The edema of saline treated rats was measured as an increase of 176 + 10% in weight (over unheated hind paw) and the protein extravasation was measured as an increase of 364 + 17 μg dye/paw (over unheated hind paw). By contrast, the rats having had the CRF showed an edema of only 83 + 9% (that is, less than half that of the control) and protein extravasation of 127 ± 16 μg/paw. Thus, administration of CRF significantly inhibited the inflammatory response to heat trauma. As shown in FIG. 2, administration of CRF significantly reduced the degree of dye leakage (which indicates leakage of proteins into the damaged skin) and edema.

FIG. 3 illustrates the inhibition by CRF of heat-induced tissue edema, as measured by changes in skin weight. When the paw of an untreated, anesthetized rat is placed in warm water (48° C.) for 5 min., the paw swells and this paw edema can be measured simply by weighing the heated paw skin and comparing its weight to the contralateral, unheated paw skin. If just saline (that is, isotonic salt water) is injected as the control procedure, the percent increase in weight (with respect to unheated paw) is 72%. By contrast, CRF administered at a dose of about 57 μg/kg i.v. inhibited the edema to an increase of only about 10%. This means that the edema was substantially inhibited, or almost prevented.

FIGS. 4 and 5 graphically illustrate trachea data. Rats, anesthetized with sodium pentobarbital 60 mg/kg i.p., were exposed to cotton saturated with 1% formaldehyde vapor for 10 min. The rats were then sacrificed and the segment of trachea removed (18–20 c-rings of trachea). The increase in trachea weight (indicating edema) and Evans blue dye (indicating protein extravasation) is shown in the respective figures. Compared to rats exposed to only cotton (without formaldehyde and labeled "normal" in FIGS. 4 and 5), saline treated rats showed a substantial increase in trachea weight and in Evans blue dye. By contrast, CRF at doses of 28.4 to 113.6 μg/kg i.v. (that is 6–24 nmol/kg i.v. shown on the graph of FIGS. 4 and 5) inhibited the edema and protein extravasation of the trachea.

For injections of drugs into the brain, a 21-gauge guide cannula was stereotaxically implanted into the lateral ventricle and a 28-gauge internal cannula coupled to a Hamilton microsyringe was used to deliver a 5-μl volume of drug solution to the brain. The site of injection was verified by injections of 0.5% solutions of methylene blue into the same cannula. In some experiments, blood pressure was measured from a cannulated carotid artery coupled to a Narcobiosystems strain gauge, cardiotachometer and polygraph. Mean arterial blood pressure (MAP) was calculated as ⅓ pulse pressure plus diastolic pressure.

To determine if the CRF effect was secondary to release of pituitary or adrenal hormones (which involves ACTH in the pathway), the activity of CRF was examined in hypophysectomized and adrenalectomized rats. CRF, 6 nmol/kg i.v., still exerted its inhibitory action in hypophysectomized animals. The surgical procedures associated with sham-operations and adrenalectomy made animals more sensitive to electrically stimulated NPE. Nevertheless, CRF, 6 nmol/kg i.v., also inhibited NPE in adrenalectomized animals. Thus, the inhibitory activity of CRF appears to be independent of its stimulatory effects on pituitary and adrenal function and consequently appears to be independent of its previously known property of elevating ACTH levels. Nor does the inflammation inhibition of CRF appear to be associated with its previously known ability to stimulate $\beta$-endorphin activities.

As has been known, CRF and related peptides produce hypotension in anesthetized and unanesthetized animals. CRF given s.c. 60 min. before an electrical stimulation of the saphenous nerve (in NPE) did not lower mean arterial pressure, but the degree of NPE inhibition was similar to that produced by an i.v. injection of CRF. This indicates that the inhibition of NPE by CRF is not associated with the hypotensive properties. Neither does the inflammation inhibition of the present invention appear to have any associaton with the hypotensive properties of CRF and its analogs.

The tail-flick response of rats to noxious stimuli was determined according to Janssen et al., Arzniem. Forschung 13, 502–507 (1963). The caudal 5 cm segment of the rat's tail was immersed in warm water (54° to 56° C.) and the withdrawal latency was recorded with a stopwatch at 10 min. intervals for 60 min. A cut-off time of 30 sec. was used if the rat did not withdraw its tail from the water. The cumulative latency was calculated for each group. The ability of CRF to inhibit 2-phenyl-1,4-benzoquinone (PBQ)-induced writhing was assayed by the method of Siegmund etal., Proceedings of the Society for Experimental Biology and Medicine 95, pp. 729–731 (1957). CRF was injected at 1, 10 and 100 ug/kg i.v. in a volume of 10 ml/kg to mice (N=8 per dose) 15 min. before i.p. injection of 0.25 ml of 0.02% aqueous solution of PBQ. The total number of writhes was then determined over a 5 min. period commencing 15 min. after administration of PBQ, a writhe being identified as an extension of a hind limb accompanied by constriction of the abdomen.

Normally, an anesthetized rat will reflexly pull its paw from the water, even in the anesthetized state. Treatment with CRF reduces the paw withdrawal frequency from the warm water. In mice, CRF inhibited the writhing response to PBQ with an ED50 and 95% confidence limits of 5.84 (2.8–16.56) nmol/kg. Thus, CRF not only reduces the swelling and protein leakage into the paw after heat exposure, but it also appears to attenuate the sensation of pain that accompanies heat.

In sum, neuropeptides in accordance with the present invention have the unusual properties of preventing or inhibiting the edema, protein extravasation, and perhaps the pain, of skin and mucosal membrane injuries. These highly advantageous properties for therapeutic treatment of skin or mucosal membrane inflammation do not appear to have any association with the previously known properties of these neuropeptides. The actual mechanisms underlying these actions are not clear at this time; however, practice of the invention provides a quick, direct and potent treatment substantially to prevent or inhibit the inflammatory response for patients. Treatment in accordance with the invention may be prior to a condition causing the inflammatory response (e.g., cancer patients undergoing radiation therapy, psoriasis or other skin disorder patients undergoing U.V. treatment), during such other medical treatment, or after exposure (such as cases of severe sunburn, traumatic accidental injury to tissues, fire and smoke or tear gas victims).

Although various aspects of the present invention have been described with respect to preferred embodiments thereof, it will be understood that the invention is entitled to protection within the full scope of the appended claims.

We claim:

1. A method of treating skin or mucosal membrane inflammation of a mammal comprising:
   administering an anti-inflammatory amount of a neuropeptide effective in inhibit inflammationof th eskin and mucosal membranes of a mammal, the neuropeptide consisting essentially of Corticotropin Releasing Factor, and analog thereof, or a non-toxic salt of the Corticotropin Releasing Factor or analog.

2. The method as in claim 1 wherein the anti-inflammatory amount of about 1 μg to about 200 μg per kg of mammal body weight.

3. The method as in claim 2 wherein the anti-inflammatory amount is an injected or infused dose of between about 5 to about 100 μg/kg of mammal body weight.

4. The method as in claim 2 wherein the administering is by intravenous, intradermal or subcutaneous injection.

5. The method as in claim 2 wherein the neuropeptide is administered in combination with a pharmaceutically acceptable carrier.

6. The method as in claim 1 wherein the neuropeptide is a mammalian Corticotropin Releasing Factor, sauvagine, or non-toxic salts of mammalian Corticotropin Releasing Factor or sauvagine, and the anti-inflammatory amount administered is at least about 1 μg per kg of mammal body weight.

7. A method for inhibiting an inflammatory response in the skin or mucosal membranes of a patient comprising:
   administering at least about 1 μg per kg of patient's body weight of a neuropeptide prior to, during or after the the patient's skin or mucosal membrane is exposed to heat, radiation or a noxious substance, the administered neuropeptide being effective to inhibit an inflammatory response to the exposure, the neuropeptide administered consisting essentially of Corticotropin Releasing Factor, an analog thereof, or a non-toxic salt of the Corticotropin Releasing Factor or analog.

8. The method as in claim 7 wherein the administering is prior to the patient's exposure.

9. The method as in claim 8 wherein the administering is up to about 1 hr. prior to the patient's exposure and is in conjuction with radiation or U.V. therapy.

10. The method as in claim 7 wherein the adminstering is by intravenous, intradermal or subcutaneous injection.

11. The method as in claim 10 wherein the injection is a dose of between about 1 to about 200 μg mammalian Corticotropin Relesasing Factor or sauvagine per kg of patient's body weight.

* * * * *

UNITED STATES PATENT AND TRADEMARK OFFICE
CERTIFICATE OF CORRECTION

PATENT NO. : 4,801,612
DATED : January 31, 1989
INVENTOR(S) : Edward T. Wei & Juliann G. Kiang It is certified that error appears in the above-identified patent and that said Letters Patent is hereby corrected as shown below:

In Claim 1, Col. 10, line 21, "in" should read --to-- and "inflammation of th" should read --inflammation of the--.

line 22, "eskin" should read --skin--.

line 24, "and" should read --an--.

In Claim 2, Col. 10, line 28, "amount of about" should be --amount is about--.

Signed and Sealed this

Eleventh Day of July, 1989

Attest:

DONALD J. QUIGG

Attesting Officer

Commissioner of Patents and Trademarks